United States Patent [19]

Schaeffer et al.

[11] Patent Number: 5,053,200
[45] Date of Patent: Oct. 1, 1991

[54] FLAMMABLE VAPOR ANALYZER

[76] Inventors: Matthew J. Schaeffer, 5 Oxford Dr., North Caldwell, N.J. 07006; Christopher G. Schaeffer, 34 Watchung Ave., Montclair, N.J. 07043

[21] Appl. No.: 398,747

[22] Filed: Aug. 25, 1989

[51] Int. Cl.⁵ .................... G01N 31/12; G01N 31/00
[52] U.S. Cl. ........................... 422/83; 422/93; 422/94; 73/1 G; 73/23.2; 73/23.31; 73/863.86; 138/42
[58] Field of Search ............ 73/1 G, 23.2, 23.31, 73/863.86; 422/83, 93, 94; 138/42

[56] References Cited

U.S. PATENT DOCUMENTS

| | | | |
|---|---|---|---|
| 2,437,720 | 3/1948 | Ackley | 422/94 X |
| 2,603,085 | 7/1952 | Cannon, Jr. | 422/94 X |
| 2,987,921 | 6/1961 | Kraftson | 73/863.12 |
| 3,106,843 | 10/1963 | Luxl | 73/863.12 |
| 3,593,023 | 7/1971 | Dodson et al. | 422/94 X |
| 3,765,247 | 10/1973 | Riggs | 422/93 X |
| 3,960,500 | 6/1976 | Ross et al. | 73/23.31 X |
| 3,999,936 | 12/1976 | Hasselmann | 422/94 X |
| 4,094,187 | 6/1978 | Navarre, Jr. | 73/1 G |
| 4,115,235 | 9/1978 | Capone | 73/23.31 X |
| 4,116,612 | 9/1978 | Melgaard | 431/76 |
| 4,128,458 | 12/1978 | Obiaya | 422/94 X |
| 4,150,495 | 4/1979 | Stern | 73/1 G X |
| 4,317,379 | 3/1982 | Oberländer et al. | 73/863.12 |
| 4,322,964 | 4/1982 | Melgaard et al. | 73/1 G |
| 4,336,721 | 6/1982 | Curtis | 73/863.11 |
| 4,336,722 | 6/1982 | Schweitzer | 73/863.12 |
| 4,342,234 | 8/1982 | Bernath | 73/863.12 |
| 4,379,412 | 4/1983 | Wood | 73/863.24 |
| 4,418,723 | 12/1983 | Koni et al. | 138/42 |
| 4,441,356 | 4/1984 | Bohl | 73/23.2 |
| 4,506,426 | 3/1985 | Nakamura et al. | 138/42 X |
| 4,545,235 | 10/1985 | Barnett | 73/1 G |

Primary Examiner—Robert J. Warden
Assistant Examiner—Stephanie Blythe
Attorney, Agent, or Firm—Mathews, Woodbridge & Collins

[57] ABSTRACT

An apparatus is provided for the analysis of flammable vapors in an industrial application, such as a solvent drying operation or the like. The apparatus continuously withdraws and returns a sample of gas from the process, separates the sample into a primary portion and a secondary test portion, tests the flammability of the test portion and recombines the test portion with the primary sample, which has been restricted to create a pressure differential enabling the flow of the test portion through the testing procedure.

19 Claims, 7 Drawing Sheets

FLAMMABLE VAPOR ANALYZER

FIELD OF THE INVENTION

The present invention relates to an apparatus for the analysis of the flammable vapor content in industrial operations, such as solvent drying operations and the like.

BACKGROUND OF THE INVENTION

Under applicable safety codes, the National Fire Codes Standards for Ovens and Furnaces NFPA, industrial ovens and dryers may operate with a concentration of flammable components of up to twenty-five percent (25%) of the lower flammable limit (LFL). In fact, an exception within the code allows operation at up to fifty percent (50%) of the LFL where a continuous vapor concentration indicator and a controller are provided.

In practice, however, most industrial ovens and dryers typically operate with concentrations of flammable components at approximately ten percent (10%) of the LFL. The fact that the typical industrial level is much lower than allowable is caused by practical situations where the covering area heated, the thickness of the coating being dried, the speed of the operation or the width of the process web are always operating at less than design. Since such low levels indicate greater fire safety in the operation, there has been little or no impetus to increase the concentration levels.

Within recent years, however, laws have been enacted to prohibit pollution, and to control the emission of volatile organic substances. Typically, state and federal laws and regulations require that the release of organic substances into the atmosphere be reduced or even totally stopped. Solvent drying processes, therefore, require that their exhaust be controlled by a solvent absorption system or an incinerator so that all organic solvent vapors are either collected for reuse or are destroyed by incineration.

Addition of an incinerator or solvent recovery system to a solvent drying process involves initial capital costs and higher operating costs. These costs are directly related to the quantity of gas handled by the abatement system. In order to make the design of an abatement system as economical as possible, one principal objective in the design of the system is to reduce the amount of air handled by the system. A system design, therefore, that allows an increase in the solvent concentration from ten percent (10%) to thirty percent (30%) of the LFL reduces the airflow to one-third of the previous flow rate. The capital cost for an abatement system would be reduced to less than one-half, and the operating costs would be reduced to about one-fifth for such a system.

Operating within the economic requirements of an abatement system, therefore, mandates operation at higher concentrations of solvent vapors. Such operation, however, reduces the margin of safety and requires a higher reliability and accuracy from a solvent vapor analyzer to conform to the law.

To insure accuracy and reliability, a solvent vapor analyzer should meet the following requirements:

1. The response time should be very fast, and the analysis of a sample should be available in two seconds or less. The response may be longer, if the particular industrial application monitored will not approach the flammable limit faster than the solvent vapor analyzer can control or shut down the process.

2. The analyzer indicator and alarms should be accurate over wide changes in solvent composition.

3. None of the vapor in the sample should be allowed to condense. All vapors follow the scientific law of partial pressure and have a specific vapor concentration per temperature curve. When the vapor is sampled from a particular industrial application at some elevated temperature, the vapor sample should be heated so that the sample does not approach its dew point within the analyzer. Operation of a solvent vapor analyzer above the vapor flash point is usually sufficient. When other constituents, like plasticizers, oils and mists are present, analyzer temperatures close to or at the dryer operating temperature are typically required.

4. Such high temperatures do not protect the sample system from the fouling by polymer products that varnish and gunk the flow components. The flow components, therefore, should then be easily removable for cleaning and all of the passages should be accessible and as large and easy to clean as feasible.

5. The vapor analyzer system and all of its component parts must be limited in number and simple in design in order to provide the highest reliability.

6. The design should meet all code requirements as found in the National Fire Protection Association, NFPA 86 Standard for Ovens and Furnaces, and NFPA 70 National Electrical Code; and American National Standard ANSI/ISA-S.12.13, Performance Requirements, Combustible Gas Detectors.

7. The design should be reliable and operate with a fail-safe design.

Solvent vapor analyzers in industry today use a variety of detectors. The flame ionization detector uses a hydrogen flame where the sample is injected into the burner and the carbon atoms present in the flame produce a measurable ion current utilizing a high voltage and an electrometer. The signal present in the detector is related to the concentration of carbon atoms. Instruments using the flame ionization principle are the Ratfisch and Bernath Atomic. These two instruments are similar in the detector design. The Bernath Atomic mounts at the sample location and the Ratfisch uses a long, heated sample line.

These flame ionization detectors were designed to perform hydrocarbon analysis and were intended to measure parts per million of hydrocarbons, but they have been used in monitoring flammable vapors. Flame ionization detectors have two serious drawbacks. Most important is the fact that they require recalibration whenever the solvent mixture is changed. The calibration is then correlated to percentage of flammable limit from parts per million hydrocarbon or carbon. This correlation is affected by the carbon molecular bonds and the presence of oxygen and other elements in the molecule causing a calibration shift with solvent formulation changes. Secondly, these flame ionization detectors employ pumps to inject a sample through capillaries into a hydrogen flame. This kind of flow system is susceptible to plugging and maintenance problems, particularly in industrial applications such as solvent drying and the like.

Sensors using the principle of catalytic combustion are frequently used in area monitoring. Their use in process monitoring is limited by their susceptibility to poisoning and deterioration by "catalytic poison,"—a group of substances that either coat or corrode the bead catalytic element. Such substances are frequently found in drying operations. To guarantee that the catalytic sensor is working properly, frequent calibration tests must be run. Even so, under certain circumstances a sensor can fail within hours and the only way to know if it has failed is by testing it with a known concentration of gas. Catalytic sensors do have a better cross calibration accuracy than the flame ionization detectors. This deficiency is addressed in U.S. Pat. Nos. 4,116,612 and 4,322,964.

Infrared spectrophotometer systems also require calibration when solvent mixtures are changed. They are not well suited for industrial applications such as oven monitoring because maintenance of the optics, which require frequent alignment and cleaning, is excessive in such applications and high temperature operation is limited.

A flame temperature analyzer, such as those manufactured by Control Instruments, Inc. uses the principle of incineration. A small pilot flame inside an explosion proof cell is continuously exposed to the sample. When the sample is air, a temperature detector indicates the heat released from the small pilot flame. When the sample contains flammable vapors, the temperature detector produces a signal in proportion to 0–50% of the lower flammable limit. The characteristics of the sensing flame detector are such that the signal produced is proportional for the lower flammable limits of a wide range of solvent vapors. The flame temperature analyzer, then, is accurate for measuring the percentage of the lower flammable limit even when the solvent vapor composition is changed.

A typical prior art flame temperature analyzer meets all of the requirements for accuracy, but has been limited in its response time because its remote location has required the use of heated sample lines which create a sample response delay. Further, the sample filter of the prior art flame temperature analyzer must filter the whole of the sample flow. Such filters, therefore, require large volumes, slowing sample delivery and are subject to frequent replacement in applications where dust or gunking is prevalent. The use of individual parts for each function typically creates a piping jungle and makes maintenance difficult thereby reducing reliability. The detector principle itself, however, is simple and reliable. It is, therefore, an object of the present invention to provide the improvements needed to enable a device with the accuracy and reliability of the flame temperature analyzer to be employed for the safe operation of processes using flammable vapors.

The prior art appears to disclose no unitary apparatus for scientifically determining with accuracy and reliability the LFL in processes that use high flash point solvents or contain low vapor pressure sample components that foul an analyzer. Such solvents and sample components are found in industrial applications for the making of vinyl tile and sheet goods, masking tape and web offset printing.

U.S. Pat. No. 4,336,721 entitled "GAS ANALYZER" discloses a heated analyzer, mountable on a duct, which uses an aspirator for sucking in the sample. This gas sampling apparatus uses an inlet tube, a nozzle through which the gas sample is metered. The sample is then drawn past the cell by the aspirator. The apparatus is heated above 430° C. to avoid the accumulation of deposits and below 704° C. to prevent the slagging of molten ash on the surfaces of the cell. The flow system is a simple once-through arrangement. The detector output is not subject to change when the flow changes, since it operates on the partial pressure of oxygen. The apparatus works well with its self cleaning objectives but does not appear to be appropriate for solvent vapors because it operates at temperatures that would decompose solvent vapors which should cause a loss of reading and accuracy.

U.S. Pat. No. 4,336,722 entitled "METHOD AND APPARATUS FOR SAMPLING WASTE GASES" describes a similar device in which an aspirator is used to draw the sample from a source. The exhaust of the aspirator is discharged through a concentric tube in the center of the sample probe. The object of this probe and apparatus is to cool and condense the sample so that vapor is removed and only gases are delivered to the gas monitor. The adiabatic cooling chamber and the discharge tube inside the sample probe are means for obtaining the greatest sample cooling which is inappropriate for the analyzer specifications.

Additional patents using aspiration or heated probes are inappropriate for the present application. U.S. Pat. No. 4,379,412 is a high temperature probe with blowback means for clearing the probe and filter. U.S. Pat. No. 3,106,843 is a steam aspirated sample probe requiring downstream condensation for operation, similar also to U.S. Pat. No. 2,987,921 where water washes the sample probe then a steam aspirator draws and cleans the sample. U.S. Pat. No. 3,593,023 also uses a condenser and aspirator. All these devices are believed to be inappropriate for the needs of the present invention.

U.S. Pat. No. 4,128,458 entitled "COMBUSTILE ELEMENT AND OXYGEN CONCENTRATION SENSOR" utilizes divided flow to operate an oxygen cell and a catalytic combustible cell. The flow was divided so that air may be added to the combustible sample to supply the oxygen required for the operation of the catalytic oxidation of the sample. A third conduit serves to carry extra sample gas to the aspirator as a means to load the aspirator and reduce the flow variations through the two detector cells. This third conduit produces no regulation because its shunting action proportionally supplies a volume of sample to meet the demand requirements of the aspirator. A similar effect could be obtained by reducing the size of the aspirator.

U.S. Pat. No. 4,317,379 entitled "PROCESS AND APPARATUS FOR THE CONTINUOUS WITHDRAWAL OF SPECIMENS FROM A CURRENT OF A CRUDE GAS FOR THE PURPOSE OF GAS ANALYSIS" preconditions the crude sample by cooling. The condensate is heated and ejected back into the sample source using a steam ejector. A branch of the high pressure sample is filtered, then pressure reduced for the analyzer. This is a reconditioning and sample cleaning apparatus whose function would destroy the accuracy of a solvent vapor analyzer.

U.S. Pat. No. 4,342,234 entitled "APPARATUS FOR EXTRACTING HOT GAS SAMPLE FROM A CHAMBER AND FOR FEEDING THE SAMPLE TO AN ANALYZER" utilizes a chamber and a sample probe surrounded by a heating jacket leading directly to a heated analyzer. This analyzer, known commercially as the Bernath Atomic utilizes a mechanical pump, capillaries for sample injection and sample bypass and a flame ionization detector. The flame ionization detector is seriously affected by changes in solvent composition. The capillaries are subject to fouling and the mechanical pump is complex, therefore the requirements for accuracy and reliability are not believed to be met.

U.S. Pat. No. 4,116,612 entitled "GAS MONITOR SYSTEM" is a self-check system to frequently introduce test gas into the gas monitoring system to determine whether the analyzer readings are in or out of calibration.

U.S. Pat. No. 4,322,964 entitled "GAS ANALYZER CALIBRATION APPARATUS" is a fluid gate on the sample probe that enables the introduction of calibration gas as outlined in U.S. Pat. No. 4,116,612. The purpose of this apparatus is to prove that the solvent vapor analyzer is accurate; if not the process is shut down and the analyzer malfunction alarmed. The need for apparatus of this design is deleted when the sample system and the detector perform accurately and reliably as found in our novel apparatus.

SUMMARY OF THE INVENTION

According to the present invention, there is disclosed an apparatus for analysis of the flammable vapor content in the gases from an industrial application, such as a solvent drying operation or the like. The apparatus comprises a sampler for continuously withdrawing and returning a sample flow of gas from the industrial application. A conduit separates the sample flow into a primary sample flow and a secondary sample flow. The secondary sample flow includes a flow of a test portion of the gas to be measured for flammable vapor content. The test portion is directed to a chamber wherein the flammability of the test portion is measured for flammable vapor content. A secondary flow restrictor is provided to limit the secondary sample flow. A conduit returns the secondary sample flow, comprising the test portion, to the primary sample flow which is connected to an aspirator. A pressure differential created by a primary restrictor enables the flow of the secondary sample flow, comprising the test portion, to be directed through the test portion.

DETAILED DESCRIPTION OF THE PRESENT INVENTION

In order to provide fast and accurate analysis of the flammable vapor content in exhaust gases from solvent drying operations and the like, the analysis should be made as quickly as possible. In practice, one of the best ways to obtain fast results is to mount the apparatus directly on the ductwork of a solvent drying operation or the like and draw samples directly from the process into the testing portion of the apparatus.

Figure 1:
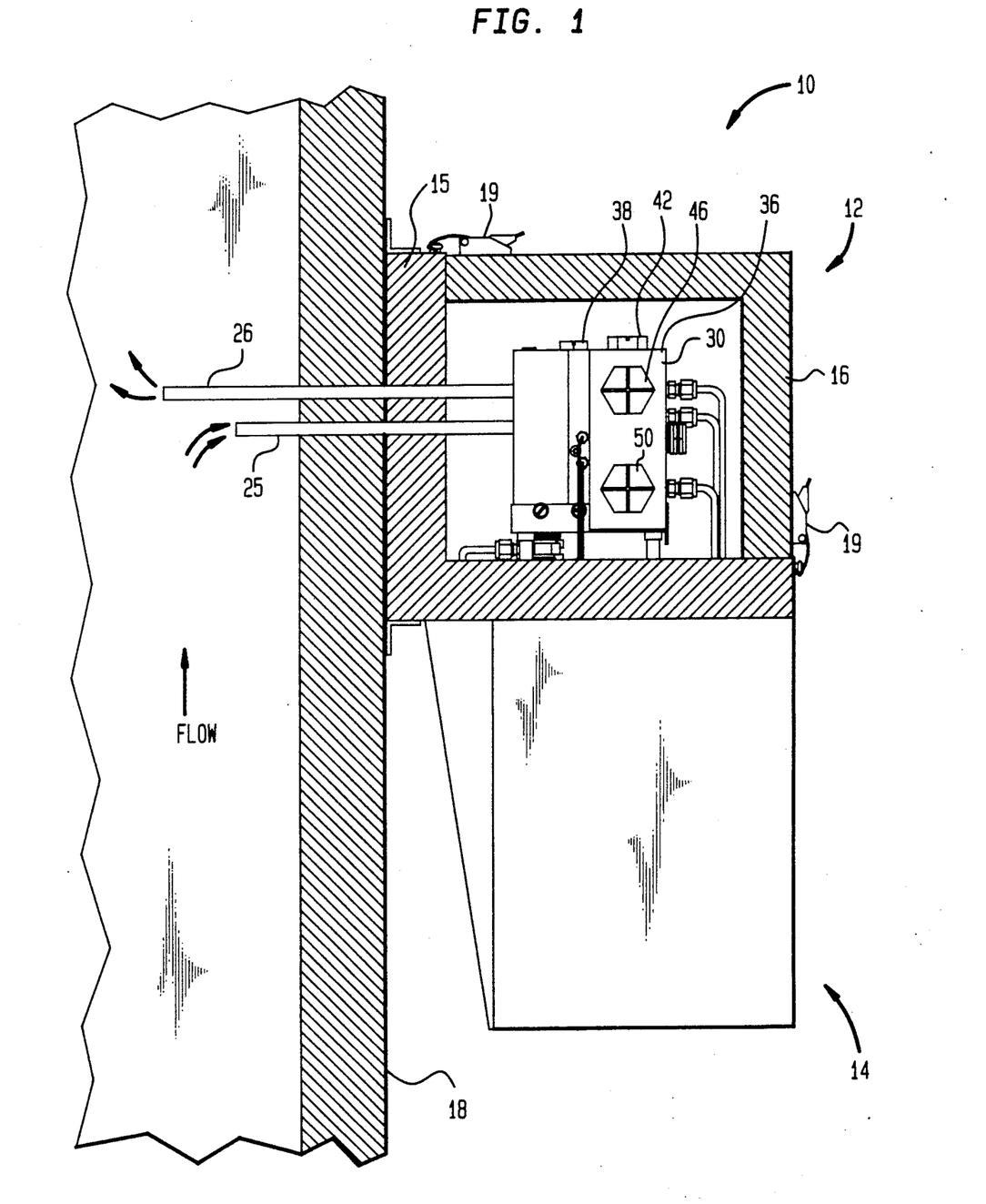
FIG. 1 shows an elevation, partly in section, of the preferred embodiment.

This type of mounting, shown in FIG. 1, eliminates the need for long sample lines which would typically have to be heated and which would result in delay.

FIG. 1 shows the analyzer 10 including a testing portion 12 and a control portion 14 as the analyzer 10 might appear in its mounted position on a vertical ductwork 18 of a solvent drying operation or the like. The ductwork 18 is pierced only by incoming sample line 25 and outgoing sample line 26. Gas is drawn from the ductwork 18 and is conveyed into the testing portion 12, shown partially cut-away, by incoming sample line 25, and returned by outgoing sample line 26 in the direction of the arrows. As seen in FIG. 1, a portion of a cover 16 that encloses the remainder of the testing portion 12 is removable for access to the test apparatus itself, and its serviceable parts. The cover 16 is fastened to a fixed housing 15 via conventional mounting clips 19.

Figure 2:
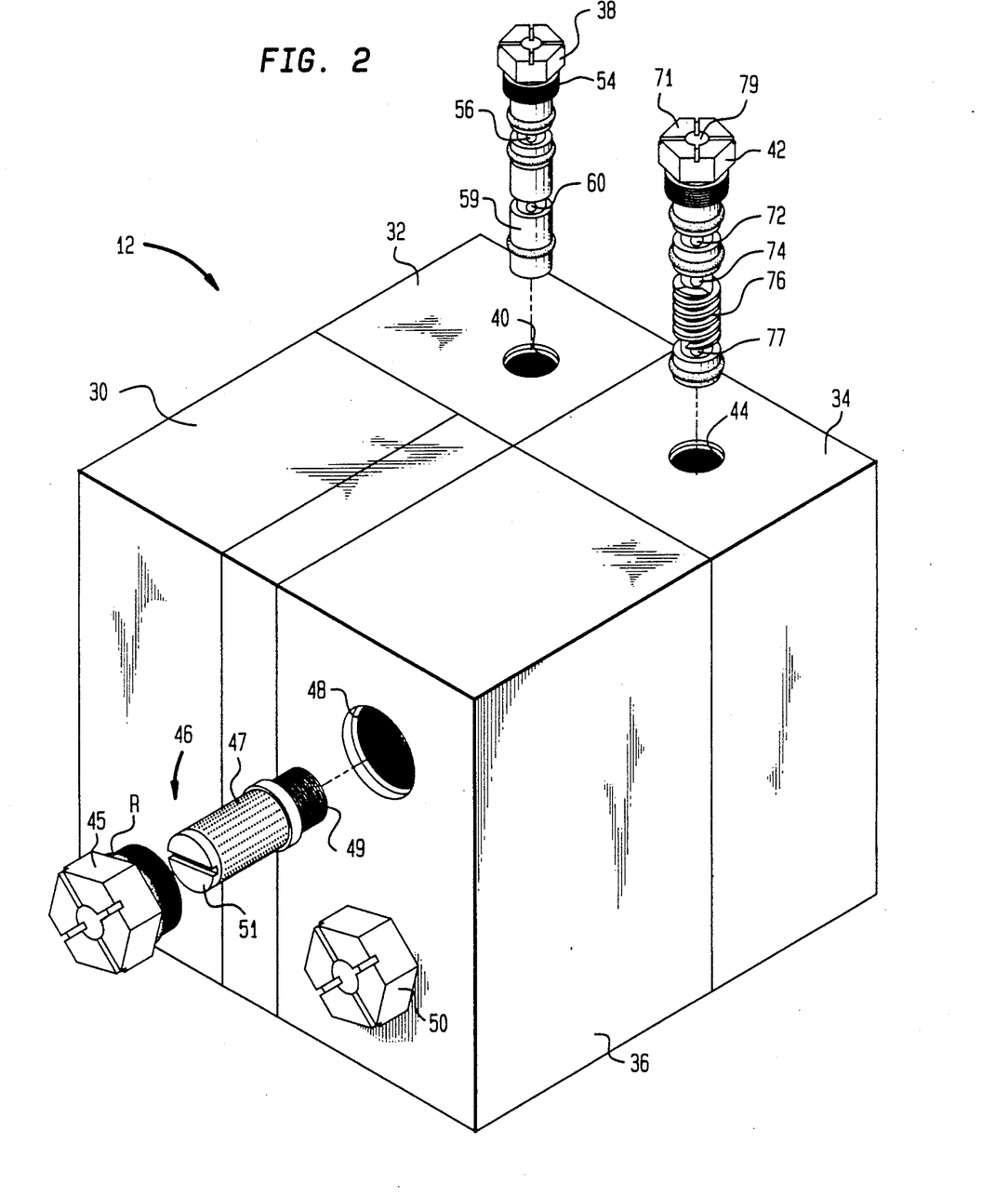
FIG. 2 shows an exploded pictorial view of the sampling and testing components of the preferred embodiment.

As seen in FIG. 2, the testing portion 12 includes a test block assembly 30 including an aspirator block 32, a restriction block 34, and a burner block 36. An aspirator assembly 38 is threaded into a bore 40 in block 32. A restriction assembly 42 is threaded into a bore 44 in block 34. An outlet filter/arrestor assembly 46 is mounted in a bore 48 in burner block 36. An inlet filter/arrestor assembly 50, identical to assembly 46, is mounted in a similar bore (not shown) in burner block 36.

Figure 3A:
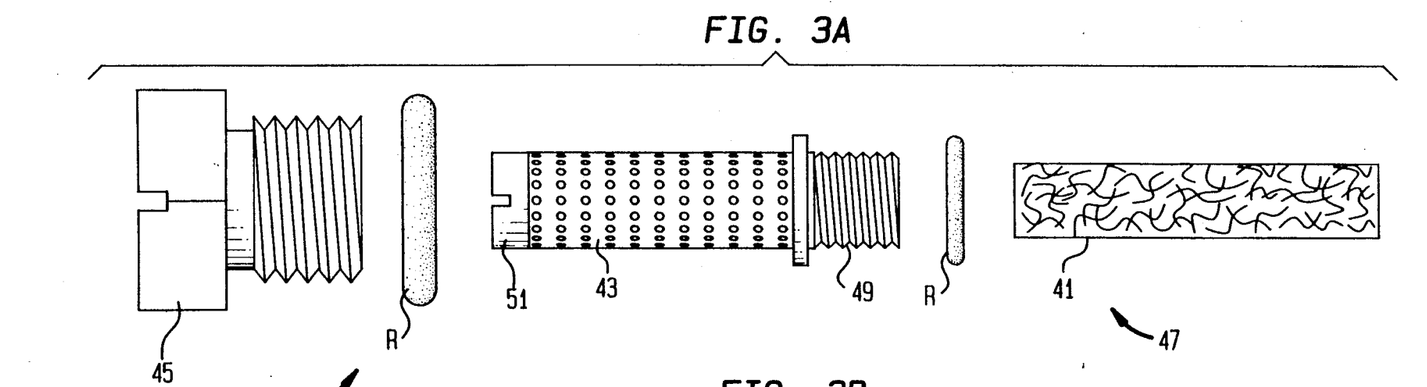
FIG. 3A is an exploded view of a portion of the preferred embodiment.
Figure 3B:
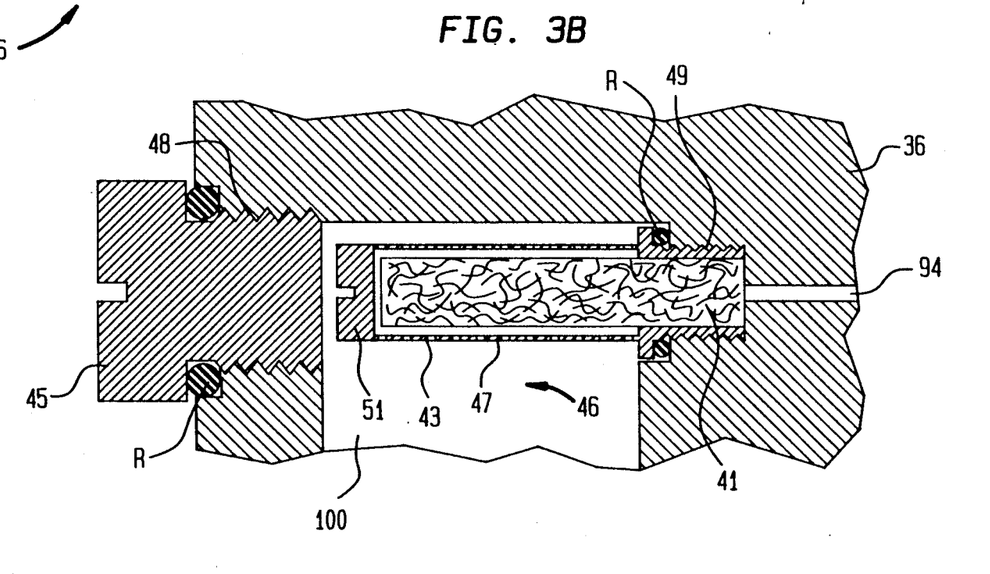
FIG. 3B is a cross-sectional view of the device shown in FIG. 3A.

A burner test chamber 100 (FIGS. 3B, 6) extends between filter/arrestor assemblies 46 and 50. Assemblies 38, 42, 46 and 50 are accessible for easy removal from block assembly 30 for cleaning and performing other types of maintenance when necessary.

The outlet filter/arrestor assembly 46 (FIGS. 2, 3A, 3B) includes a filter/arrestor 47 having a threaded nipple 49 fixed at one end and a slotted head 51 fixed at the other end. Assembly 46 further includes a threaded plug 45 for closing the bore 48 in block 36. Filter/arrestor 47 includes a flame arrestor screen 43 formed from a hollow metal cylinder having a plurality of small openings therein. A gas filter 41, in the form of a roll of porous material, snugly fits into the interior of screen 43 and nipple 49. The inlet filter/arrestor assembly 50 is similar in structure to outlet filter/arrestor assembly 46. A passage 94 in blocks 36 and 34 extends from the end of bore 48 (FIG. 3B) to bore 44 (FIG. 4B). A similar passage 91 extends from the bore in which assembly 50 is housed (FIG. 6) to bore 44 (FIG. 4B). O-rings R are provided on filter/arrestor 47 and plug 45 for appropriate sealing.

Figure 4A:
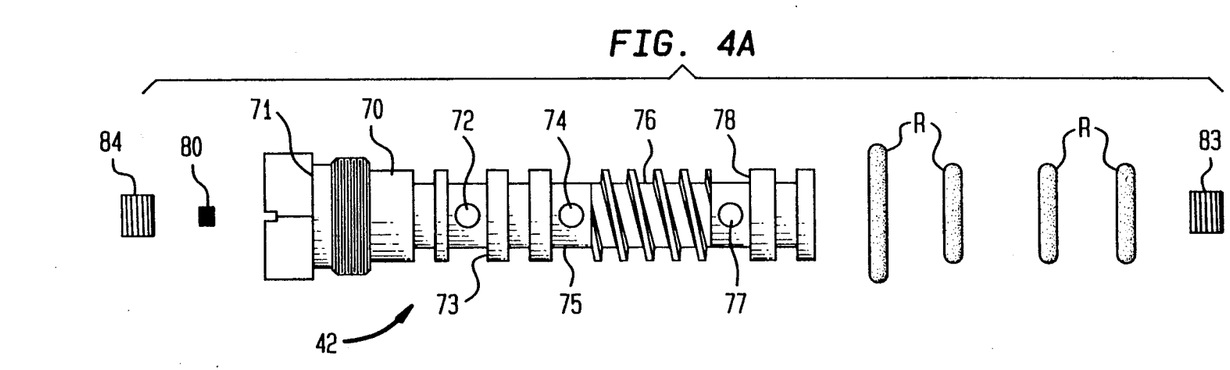
FIG. 4A is an exploded view of a portion of the preferred embodiment.
Figure 4B:
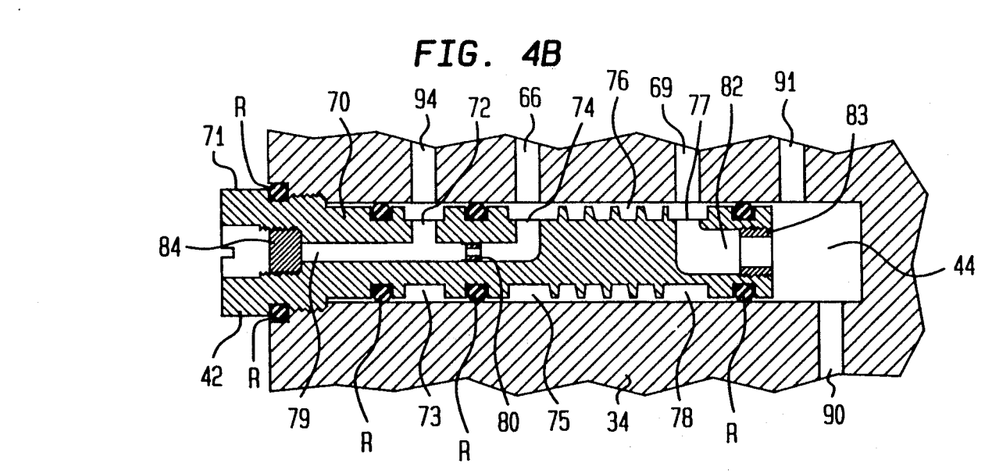
FIG. 4B is a cross-sectional view of the device shown in FIG. 4A.

The restriction assembly 42, shown in detail in FIGS. 4A, 4B, includes a body portion 70 having a threaded head 71, an opening 72 located in an annular channel 73, an opening 74 located in an annular channel 75, a spiral channel 76, and an opening 77 located in annular channel 78. Assembly 42 includes a first passage 79 that extends through head 71 to opening 74 and includes a branch that communicates with opening 72. A second passage 82 extends from opening 77 to a threaded opening in the end of body 70 that receives a threaded restriction orifice 83. A second restriction orifice 80 is threaded or otherwise fixed in passage 79. A plug 84 is threaded into head 71 to plug passage 79 after orifice 80 is assembled therein. O-rings R are mounted on the exterior of assembly 42 to provide seals with the inside surface of bore 44.

As seen in FIG. 4B, block 34 has a plurality of internal passages 90, 91 that terminate near the bottom of bore 44. Passages 69, 66, 94 are also formed in block 34 to communicate with bore 44 at positions such that the passages are aligned with channels 78, 75, 73, respectively. Passage 69 extends to the outside surface of block 34 where it is joined with incoming sample line 25. Passage 94 extends between bores 44 and 48. Passage 91 extends from bore 44 to assembly 50 (FIG. 6). Passage 90 extends from bore 44 to the exterior surface of block 30 where it joins with calibration line 93 that in turn is connected to a calibration unit 92 through a valve 96. Passage 66 extends from bore 44 to bore 40 (FIG. 5B).

Figure 5A:
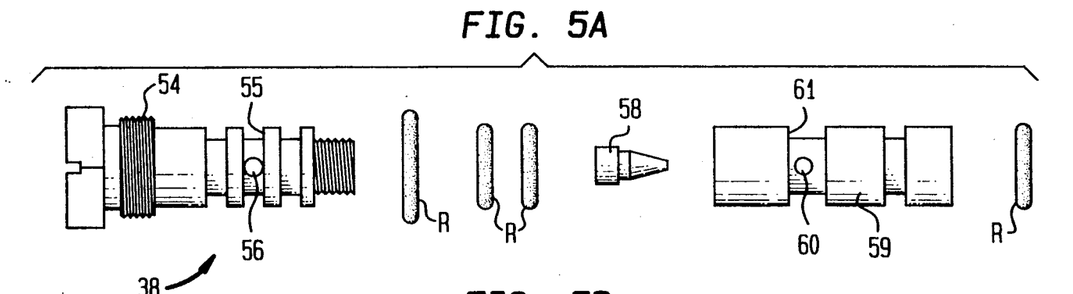
FIG. 5A is an exploded view of another portion of the preferred embodiment.
Figure 5B:
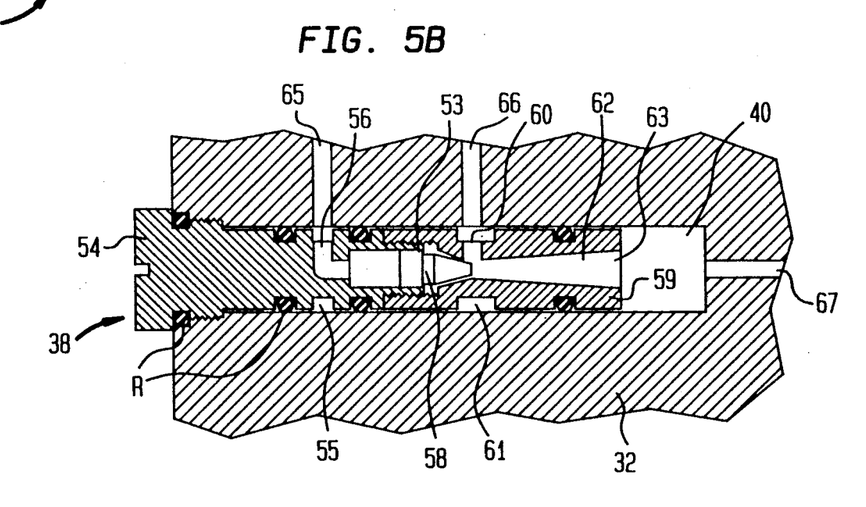
FIG. 5B is a cross-sectional view of the device shown in FIG. 5A.
Figure 6:
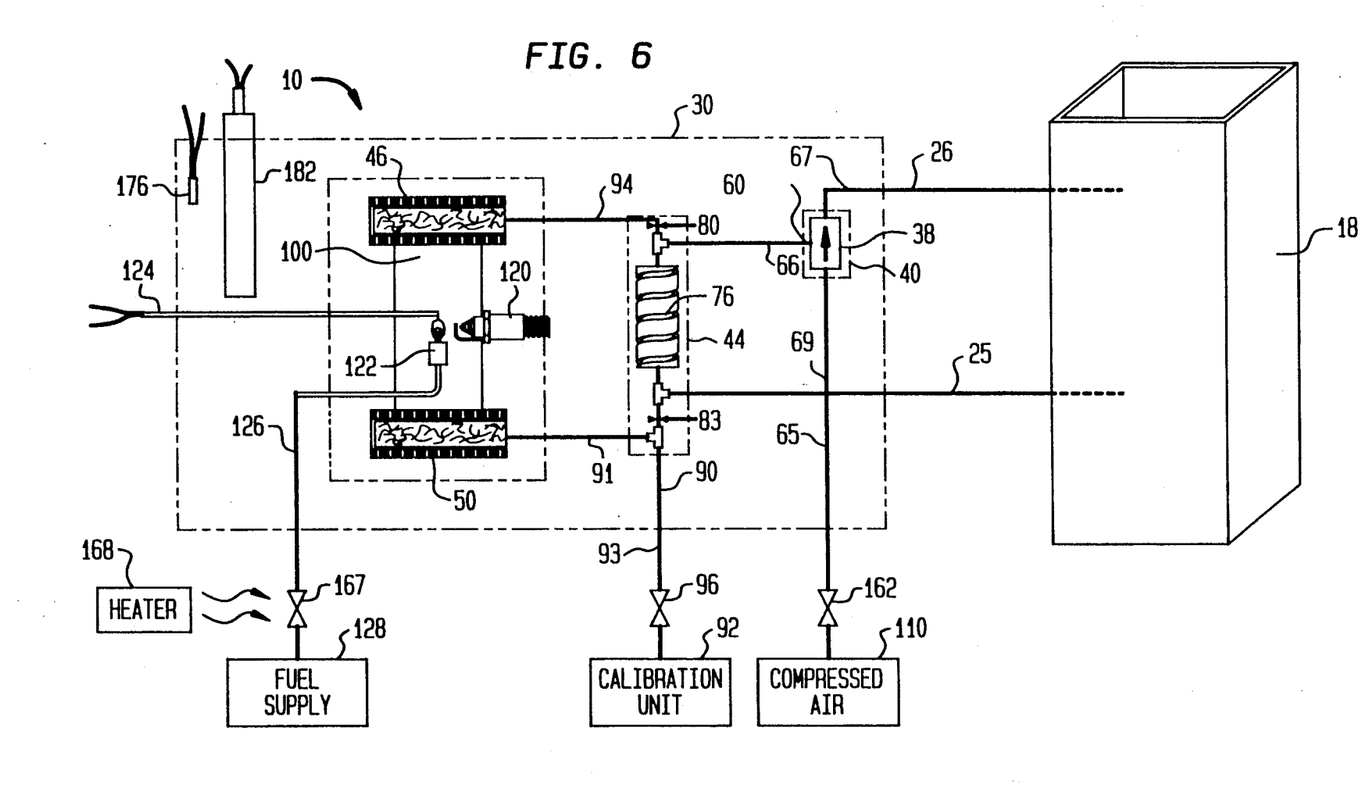
FIG. 6 is a schematic diagram showing pneumatic and electric elements of the preferred embodiment.

The aspirator assembly 38, shown in detail in FIGS. 5A, 5B, includes a threaded head 54 having a compressed air inlet 56 located in annular channel 55, and a chamber 53 for receiving nozzle 58. A venturi section 59 is threaded onto head 54 and includes a venturi inlet 60 located in annular channel 61. An expansion passage 62 extends through section 59 to complete a conduit from the inlet 56 through nozzle 58 past inlet 60 to the exit opening 63. O-rings R are properly placed along the exterior of assembly 38 to form seals with the interior surface of bore 40. A passage 67 extends through block 32 from the bottom of bore 40 to the outgoing sample line 26.

FIG. 6 is a schematic flow diagram useful in understanding the operation of the present invention. Incoming sample line 25 is shown extending from the interior of ductwork 18 to passage 69 in block 30. The passage 69 is shown schematically as communicating with bore 44 and intersecting with the bottom end of the spiral channel 76 and passages 90, 91. Passage 91 terminates at the inlet to filter/arrestor assembly 50. The passage 94 is shown schematically as extending from the outlet of arrestor/filter assembly 46 to the bore 44 where it communicates with the top end of the spiral channel 76 and passage 66 via the restriction orifice 80. The passage 66 intersects with the top end of the spiral channel 76 and the orifice 80, and it communicates with bore 40 where it is connected to the venturi inlet 60 of assembly 38. Compressed air supply 110 is connected to passage 65 via valve 162. The output end of nozzle 58 in assembly 38 is connected to passage 67 which joins outlet line 26.

The test chamber 100 has a spark plug 120 mounted adjacent a flame jet 122 which in turn is mounted just below a thermocouple 124. Spark plug 120 may be energized in a conventional manner to ignite flame jet 122. A fuel passage 126 is connected between a gas fuel supply 128 and the flame jet 122.

The block 30 is heated by a main heater 182 that extends therein. Heat is applied to block 30 to insure efficient operation and to prevent cooling and unwanted condensation of the gases flowing in the block 30. A main heater thermocouple 176 is embedded in block 30 to provide a signal to control the operation of heater 182 in a manner to be described below.

Figure 7:
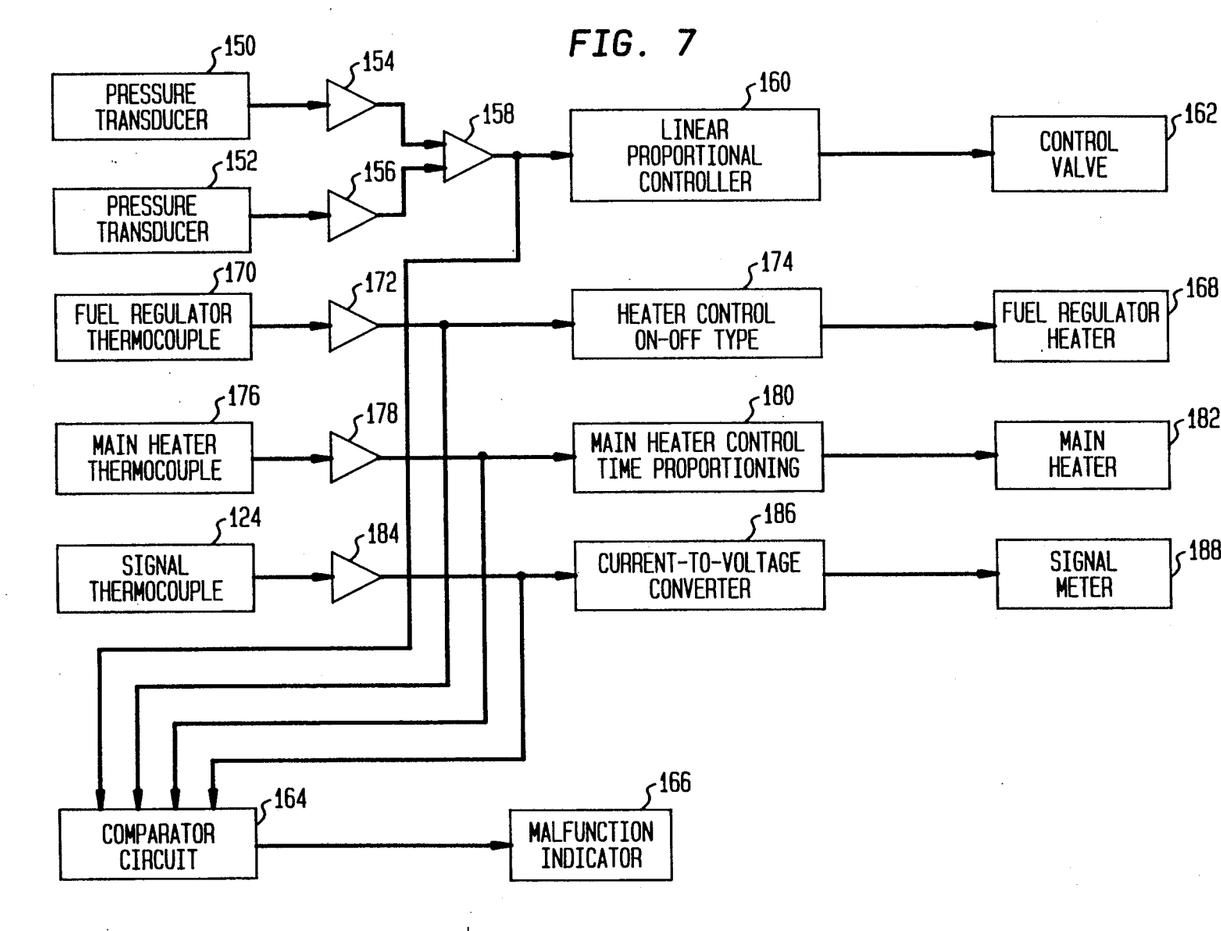
FIG. 7 is an electrical block diagram of a portion of the preferred embodiment.

FIG. 7 shows a block diagram of an electronic control network. A pressure transducer 150 has an output which is a function of the pneumatic pressure in passage 94. A second pressure transducer 152 has an output which is a function of the pressure at the top of spiral chamber 76. The output of transducers 150 and 152 are first amplified in amplifiers 154 and 156, respectively, and then fed to the inputs a differential amplifier 158.

The output of differential amplifier 158 will be proportional to the difference between the voltages applied at the inputs thereof. As such, the output of amplifier 158 will be a measure of the difference in pressure between passage 94 and the top end of spiral channel 76. This difference in pressure is produced across the orifice 80. As is well known, this difference in pressure will be a measure of the pneumatic flow rate through orifice 80. The output voltage of differential amplifier 158 will, therefore, be an indication of the flow rate through orifice 80. The output of differential amplifier 158 is fed to the input of linear proportional controller 160 whose output is used to control valve 162. The flow rate across orifice 80 may, therefore, be controlled by the position of valve 162, which in turn, adjusts the flow of compressed air from source 110 to aspirator assembly 38. In turn the aspirator assembly 38 will provide the pneumatic power needed to draw gas samples from ductwork 18 via line 25. As such the linear proportional controller 160 operates to raise and lower the pressure to aspirator assembly 38 to automatically maintain a constant sample flow which automatically corrects pressure abnormalities or pressure drops created by the fouling of the sample lines and passages, sample orifice 80, and the filter/arrestors 46, 50.

A comparator circuit 164 has one of its inputs connected to the output of differential amplifier 158. Comparator circuit 164 will compare the voltage at the output of differential amplifier 158 to an internally stored voltage reference and generate an output signal for energizing a malfunction indicator 166, which may be an audio device such as a buzzer, horn or the like, or a visual indicator such as a light or meter.

A fuel regulator valve 167 is provided to regulate the amount of fuel being supplied to jet 122. The valve 167 has connected thereto a fuel regulator heater 168 that heats gases passing through valve 167. A conventional fuel regulator thermocouple 170 is mounted in a conventional manner in valve 167 for measuring the heat of the fuel passing therethrough. The output of a fuel regulator thermocouple 170 is amplified by an amplifier 172 and then applied to the input of the heater control 174 which is preferably of the on-off type. The output of heater control 174 will regulate the fuel regulator heater 168 to maintain the temperature of the fuel at the output orifice of valve 167 at a predetermined value.

The main heater thermocouple 176 senses the temperature in the block 30 and provides an output signal that is amplified in amplifier 178 and then inputted to the main heater control 180. Main heater control 180 is preferably of the time proportioning type wherein a main heater 182 is turned on and off in anticipation of a temperature increase or decrease according to a timed function. The signal thermocouple 124 is located in chamber 100 just above the flame of jet 122. The temperature of the gases just above the flame of jet 122 will be a measure of the amount of fuel burning in chamber 100. The fuel burning in chamber 100 will normally be a result of only the fuel supplied via fuel valve 167. However, when combustible gases appear in the ductwork 18 and are supplied to chamber 100 in addition to the fuel normally supplied by fuel valve 167, there will be additional heat produced in chamber 100 which will raise the temperature therein. As such, changes in the output of transducer 124 will be an indication of the amount of combustible gases in ductwork 18 assuming, of course, that the fuel supply via valve 167 remains constant. The output of thermocouple 124 is supplied to amplifier 184 and then to current-to-voltage converter 186. The voltage output from converter 186 is fed to a signal meter 188 which may be calibrated to indicate the amount of combustible gases being supplied to chamber 100. The outputs of amplifiers 172, 178, and 184 are also sampled by comparator circuit 164 wherein the samples are compared to normal reference values. If an abnormal condition exists as indicated by the amplitude of the outputs from amplifiers 158, 172, 178, and 184, a signal will be sent by comparator circuit 164 to energize a malfunction indicator 166.

When compressed air from source 110 is delivered to aspirator assembly 38, gas samples will be drawn from ductwork 18 via line 25. The drawn gas sample will be split into a primary sample flow and a secondary sample flow. The primary sample flow will first pass from passage 25 into spiral channel 76 and then into passage 66.

The secondary sample flow is used as the test sample. The secondary sample flow is drawn from passage 25 into passage 91 where it is delivered to inlet filter/arrestor assembly 50 where the test sample is filtered and directed into test chamber 100. The test sample in chamber 100 will mix with the fuel at the jet 122 to alter the intensity of the flame at jet 122 just below thermocouple 124. The gases in chamber 100 are drawing through outlet arrestor/filter assembly 46, passage 94, orifice 80 and passage 66 where it is combined with the primary sample flow exiting from spiral channel 76. The combined primary sample flow and the secondary sample flow are now drawn from passage 66 by aspirator assembly 38 and returned to ductwork 18 via passage 67 and output line 26.

The output of meter 188 will be an indication of the flammable content of the gas in ductwork 18. This output may be used to take appropriate action to reduce or increase the flammable content of the gas in ductwork 18 as needed.

It is useful to periodically check the calibration of meter 188. The calibration unit 92 may be employed to perform such calibration even while the system is in operation. Also, there is no requirement that a valve be placed in the sample line 25 to cut off the sample during calibration. Calibration unit 92 would include at least a compressed air source, a source of a known mixture of air and flammable components under pressure, and a flow meter. A typical calibration procedure would begin with a "zero" calibration by transmitting compressed air from unit 92 to chamber 100 via line 93, passages 90, 91 and filter/arrestor 50 at a flow rate equal to or greater than the sample flow rate in passage 91. As such, the compressed air from unit 92 will prevent samples from ductwork is to flow in channel 91. If the flow is sufficiently large, some of the compressed air from unit 92 may also pass through orifice 83 and be transmitted through spiral channel 76 and channel 69. In any case, the compressed air transmitted to chamber 100 will produce a reading on meter 188 that will be used to provide a zero calibration point on the meter 188, i.e. a meter reading equivalent to a zero calibration of flammable components. A second calibration point on the meter 188 is acquired by turning off the compressed air source in unit 92 and transmitting from unit 92 a gas having a known concentration of flammable components mixed with air. Again, the flow rate of this mixture should be equal to or larger than the normal sample flow rate in channel 91. This known flammable mixture will burn in chamber 100 thereby producing a temperature reading via thermocouple 124. The output of meter 188 may now be calibrated based on the reading that is produced by burning only the known concentration of the mixture in chamber 100. Of course, the remaining concentration points on meter 188 will be proportionally equal to the meter reading associated with the known concentration. Normal operation of the system may now be resumed by simply closing valve 96 to disable the calibration unit 92.

Because a relatively large sample of gas is removed from ductwork 18, problems associated with the drawing of a small sample of a gas through small orifices that are easily clogged are avoided in the present invention. The large sample of gas is split to form a small test sample, called the secondary sample flow, at the very large orifice 83 (FIGS. 4A, 4B). The remaining primary sample flow passes through the spiral channel 76 which acts as a restrictor that will cause an appropriate pressure drop in the primary sample flow. The secondary sample flow passes through chamber 100 and then through orifice 80 (FIG. 4B) to be recombined with the primary sample flow. While in chamber 100, the secondary sample flow has not only been tested but has also been filtered twice by filter/arrestors 46, 50. Therefore, any clogging of the system will normally take place in the restriction assembly 42 and in particular spiral channel 76 which may be readily removed from bore 44 for cleaning and maintenance.

Obviously many modifications and variations of the present invention are possible in the light of the above teachings. For example, important but not critical to the operation of the apparatus of the present invention is primary flow restrictor or spiral channel 76 which impedes the flow of gas in the primary sample flow and creates a pressure differential between channels 75 and 78 (FIG. 4B). The most common restriction means employed in this art is an orifice of small diameter, prohibiting flow. Such an orifice could be employed in the apparatus of the present invention, but is not preferred. First, orifices, because of the small size necessary to be effective, are subject to gapping and clogging. This would be particularly true in the apparatus of the present invention where the primary sample flow is intended to be essentially unfiltered. Where filters are employed in the sampling lines, they require substantial volumes and thus slow the response time of the apparatus.

Secondly, the use of an orifice as a restriction means, particularly in the unfiltered primary sample flow of the present invention, would increase maintenance problems as such orifices are difficult to clean quickly.

Another option available is to employ an extended path in the form of a coil or loop. To extend the primary sample flow in such a manner would provide the necessary pressure differential and, because of the larger diameter, could be employed without filtering and yet would not be as subject to clogging as an orifice. Maintenance of such a loop or coil or the like would be difficult because the loop or coil or the like would be difficult to clean. Still, maintenance problems may be minimized by using disposable, replaceable parts, an expensive alternative.

In the preferred embodiment, however, the restriction means is provided by the large diameter spiral channel 76 cut in a plug within a large diameter tube, viz. bore 44. This feature has the advantage of a restrictor means with a diameter larger than an orifice, thereby avoiding clogging problems. At the same time maintenance can be simplified by the expedient of pulling the assembly 42 from the bore 44 and wiping clean the exposed spiral groove.

It should be understood, of course, that the foregoing disclosure relates to only a preferred embodiment of the invention and that numerous modifications or alternations may be made therein without departing from the spirit and the scope of the invention as set forth in the appended claims.

What is claimed is:

1. A method for the analysis of flammable vapors in a gas in an industrial application. said method comprising the steps of:
   withdrawing a sample flow of a gas from an industrial application;
   dividing said sample flow into
      a primary sample flow, and
      a secondary sample flow comprising a flow of a test portion of said gas;
   filtering said secondary sample flow to remove unwanted particles;
   testing by a suitable testing means, the flammable vapor content of the test portion of said gas;
   restricting the flow of said secondary sample flow by means of a secondary sample flow restriction means;
   combining said secondary sample flow with the primary sample flow;
   restricting said primary sample flow between the step of dividing said secondary sample flow from said primary sample flow and the step of combining said secondary sample flow with said primary sample flow, thereby creating a pressure differential enabling the flow of said secondary sample flow comprising the test portion; and
   returning the sample flow to said industrial application, 2. The method of claim 1 wherein said step of filtering further comprises the step of:
   filtering said secondary sample flow prior to testing the flammable vapor content of the test portion of said gas.

3. The method of claim 1 wherein the step of filtering further comprises the step of:
   filtering said secondary flow after testing the flammable vapor content of the test portion of said gas.

4. An apparatus for the analysis of the flammable vapor content in gases in an industrial application, said apparatus comprising:
   drawing means including means for continuously withdrawing a sample gas flow from an industrial application and returning said sample gas flow to said industrial application;
   conduit division means adapted to separate said sample gas flow into a a primary sample flow and a secondary sample flow, wherein said secondary sample flow comprises a test portion of said sample gas flow to be measured for flammable gas content;
   primary sample flow line means through which said primary sample flow is able to travel;
   secondary sample flow line means through which said secondary sample flow is able to travel;
   conduit combining means adapted to recombine said secondary sample flow and said primary sample flow, said conduit combining means being connected to said drawing means;
   first means in said secondary sample flow line;
   primary flow restriction mean in said primary sample flow line for restricting said primary sample flow between said conduit division means and said conduit combining means, thereby creating a pressure differential enabling said secondary sample flow to flow through said apparatus,
   measuring means in said secondary sample flow line downstream of said conduit division means for measuring the flammability of said test portion to determine the flammable vapor content of said test portion; and
   secondary flow restriction means in said secondary sample flow line, said secondary flow restriction means adapted to limit said secondary sample flow.

5. The apparatus of claim 4 wherein the drawing means comprises an air aspirator.

6. The apparatus of claim 5 wherein the operation of said aspirator is capable of regulating the flow of gas within said secondary sample flow.

7. The apparatus of claim 6 wherein a flow rate detector means detects the flow rate of said secondary sample flow and includes means for regulating said aspirator to regulate the flow of gas within said secondary sample flow.

8. The apparatus of claim 7 further including a compressed air source connected to said aspirator through a valve, and a linear proportional controller means connected to said flow rate detector means and said valve for regulating said aspirator.

9. The apparatus of claim 4 further comprising calibration means interconnected with said secondary sample line for selectively providing a gas of zero concentration of flammable vapor content and a gas of known flammable vapor content.

10. The apparatus of claim 9 wherein said calibration means includes a source of vapors of known concentration connected to said secondary sample flow line to provide a flow rate of said vapors of known concentration greater than the flow rate of said secondary sample flow.

11. The apparatus of claim 4 wherein the means employed to measure the flammability of the test portion is a flame temperature detector.

12. The apparatus of claim 4 wherein said filter means comprises inlet filter means upstream of said measuring means.

13. The apparatus of claim 4 wherein said filter means comprises outlet filter means in said secondary sample flow line downstream of said measuring means.

14. The apparatus of claim 4 wherein said primary restriction means comprises a modular spiral channel means wherein said modular spiral channel means is adapted to be readily removed from and replaced in said apparatus.

15. The apparatus of claim 13 wherein said secondary flow restriction means comprises an orifice, and wherein the cross-sectional area of said spiral channel is at least six times as large as the cross-sectional area of said orifice.

16. The apparatus of claim 4 wherein said filter means comprises flame arrestor means and porous material filter means.

17. The apparatus of claim 14 wherein said primary restriction means comprises a module including said spiral channel means, wherein said module is adapted to be removed from and replaced in said apparatus.

18. The apparatus of claim 12 wherein said inlet filter means comprises a module comprising flame arrestor means and porous material means, wherein said module is adapted to be readily removed from and replaced in said apparatus.

19. The apparatus of claim 13 wherein said outer filter means comprises a module comprising flame arrestor means and porous material means, wherein said module is adapted to be readily removed from and replaced in said apparatus.

* * * * *